United States Patent [19]
Onuki

[11] Patent Number: 5,681,332
[45] Date of Patent: Oct. 28, 1997

[54] LIGATION APPARATUS

[75] Inventor: Takamasa Onuki, 150 Yamashita-cho, Naka-ku, Yokohama-shi, Kanagawa, Japan

[73] Assignees: Takamasa Onuki, Kanagawa; Masayoshi Yokoyama, Tokyo, both of Japan

[21] Appl. No.: 553,177

[22] Filed: Nov. 7, 1995

[51] Int. Cl.⁶ .................................................. A61B 17/00
[52] U.S. Cl. ...................................... 606/148; 606/139
[58] Field of Search ................................. 606/139, 144, 606/145, 148, 151, 205–208; 112/169, 80.03

[56] References Cited

U.S. PATENT DOCUMENTS

| | | | |
|---|---|---|---|
| 5,217,471 | 6/1993 | Burkhart | 606/148 |
| 5,250,054 | 10/1993 | Li | 606/148 |
| 5,389,103 | 2/1995 | Melzer et al. | 606/144 |
| 5,423,833 | 6/1995 | Zauza | 606/139 |

FOREIGN PATENT DOCUMENTS 5-42161  2/1993  Japan .

*Primary Examiner*—Jeffrey A. Schmidt
*Attorney, Agent, or Firm*—Lowe, Price, LeBlanc & Becker

[57] ABSTRACT

A ligation apparatus includes an opening portion at a front end of a rod, in communication with the front end side, the left side, and the right side, having a cross section of substantially a U-shaped configuration in the direction of axis of the rod, and a mobile unit in the opening portion. The mobile unit includes a body held in a movable manner, and a thread supporting unit having the tip end protruding from the opening portion for supporting a ligature at the front end. The ligature has one end tied to the thread supporting unit of the mobile unit, and the other end translated downwards from the upper side of the mobile unit according to a predetermined direction of rotation, whereby a knot of the ligature is formed. Therefore, a ligation site can be ligated extracorporeally even if the hole puncture in a somatic layer is small.

6 Claims, 19 Drawing Sheets

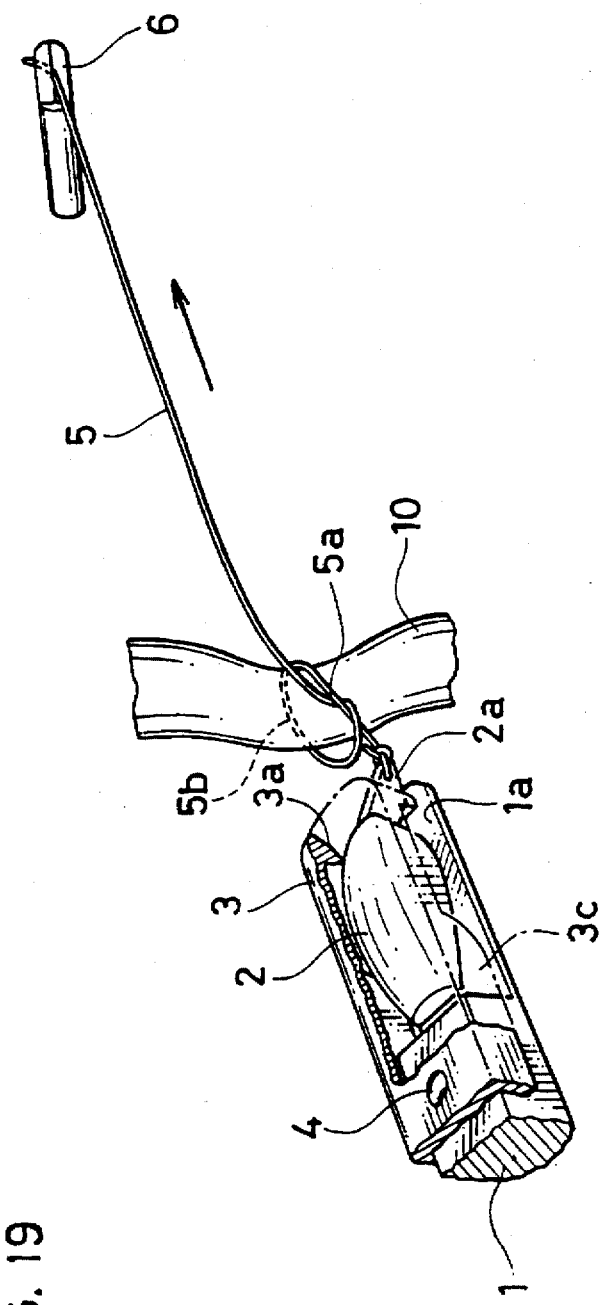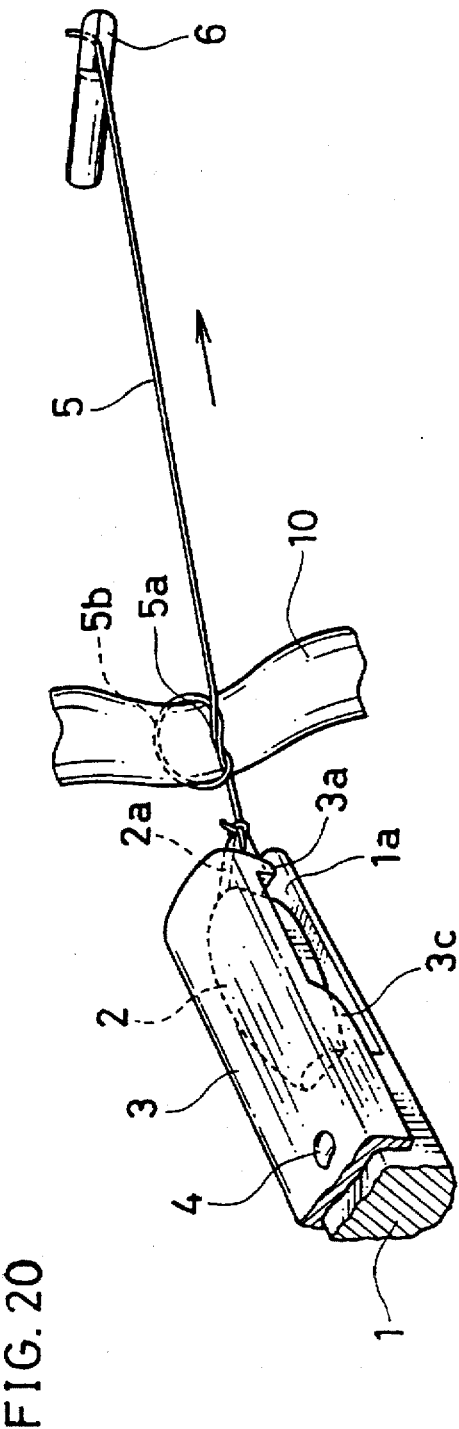

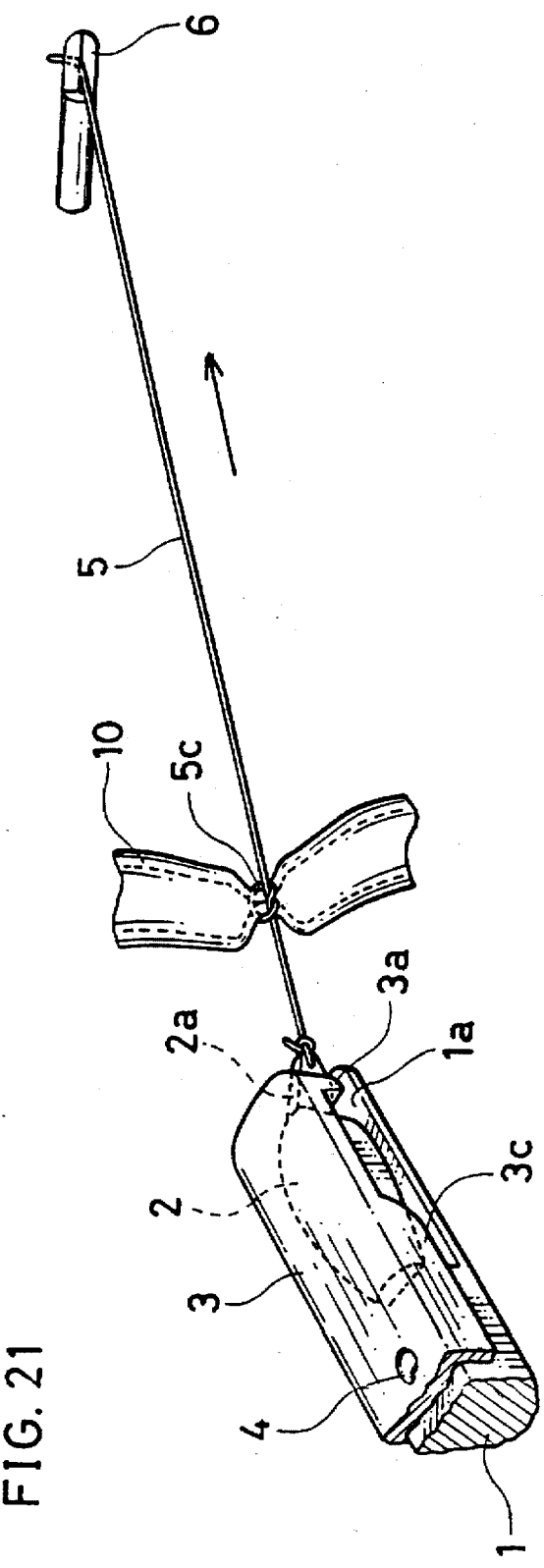
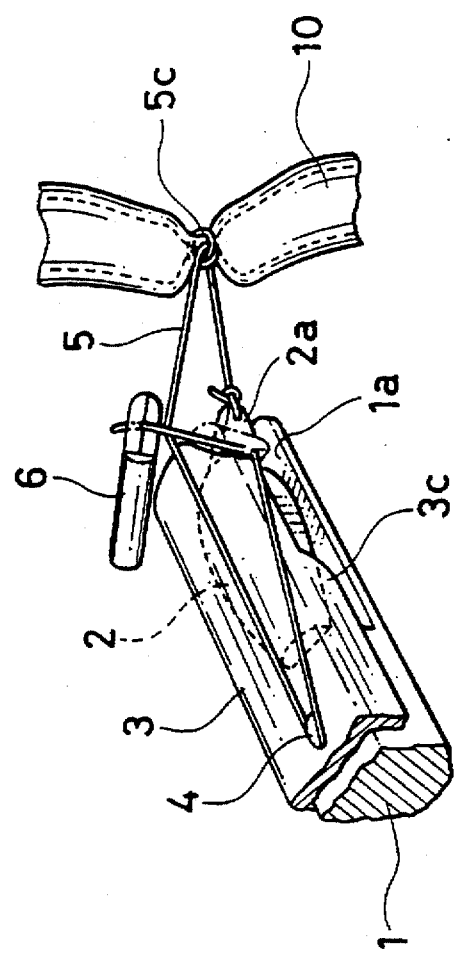
FIG. 21
FIG. 22

LIGATION APPARATUS

BACKGROUND OF THE INVENTION

1. Field of the Invention

The present invention relates to a ligation apparatus for ligating extracorporeally a site in a body cavity that is difficult to ligate.

2. Description of the Background Art

A conventional ligation apparatus is described, for example, in Japanese Patent Laying-Open No. 5-42161. This ligator will be described hereinafter with reference to FIG. 38.

The conventional ligation apparatus includes a main body 201 of the ligation apparatus and a ligature 207. Main body 201 includes an introducing section 202 and a receiving section 203. Introducing section 202 includes a hook section 202a at the front end that circumscribes a blood vessel 210, an introducing passage 202b for guiding a flexible insert member 206 towards the front end portion of hook section 202a, and a slit 202c along and in communication with introducing passage 202b, facing blood vessel 210.

Receiving section 203 includes a receiving passage 203b located on the prolongation of the line of the tip end of hook section 202a of introducing section 202 for guiding flexible insert member 206 output from the tip end of hook section 202a, and a slit 203c in communication with receiving passage 203b and orthogonal to slit 202c.

Ligature 207 is inserted into flexible insert member 206, and includes a stopper 207b which is engaged to or which is detachable from flexible insert member 206 at one end, and a knot-loop portion 207a at the other end.

Ligation of blood vessel 210 by the ligation apparatus of the above structure will be described hereinafter. Hook section 202a at the front end of introducing section 202 of main body 201 encompasses blood vessel 210 as shown in FIG. 38. Then, flexible insert member 206 is loaded into introducing passage 202b of introducing section 202.

Ligature 207 with stopper 207b at one end is inserted through flexible insert member 206. Translation of flexible insert member 206 along introducing passage 206b causes ligature 7 to be led through introducing passage 202b together with flexible insert member 206.

Flexible insert member 206 coming out from the tip end of hook section 202a is guided into receiving passage 203b of receiving section 203 located on the prolongation of the line of the tip end portion of hook section 202a. Flexible insert member 206 is inserted into knot-loop portion 207a located at the other end of ligature 207, and then pulled out from receiving passage 203 (the state shown in FIG. 38).

Knot-loop portion 207a is tied in ligature 207. Then, ligature 207 is pulled, and flexible insert body 206 is pushed back into hook section 202a. As a result, ligature 207 forms a loop at the site to be ligated of blood vessel 210 through slit 202 of introducing section 202 and slit 203c of receiving section 203. Knot-loop section 207a of ligature 207 is translated to the ligation site. The loop is gradually narrowed to ligate the encompassed blood vessel.

Then, flexible insert member 206 and main body 201 are removed outside the body. The remaining portion of ligature 207 tying the ligation site is cut, and the ligation process of blood vessel 210 is completed.

As described above, ligation of blood vessel 210 can be maneuvered extracorporeally. Therefore, ligation can be carried out readily even for a tubular organ in a body cavity which cannot be passed through a loop.

However, it is to be noted that main body 201 of the conventional ligation apparatus shown in FIG. 38 has an overall flat configuration. It is necessary to load flexible insert member 206 together with ligature 207 into hook section 202a having a great radius of curvature. Therefore, the body of a conventional ligation apparatus is inevitably increased in width as shown in FIG. 38.

This means that the puncture wound made in the wall of the body for inserting the main body of the ligation apparatus is not small, exhibiting a noticeable width in a predetermined direction. This punctual wound must be sutured at the end of the surgery, imposing an appreciable burden on the patient.

Furthermore, the ligation process necessitates flexible insert member 206 to be translated for a predetermined distance from the tip end of hook section 202a of introducing section 206 into receiving passage 203b of receiving section 203. Therefore, the tip end of flexible insert member 206 must be precisely aligned with receiving section 203. Furthermore, there are some cases where flexible insert member 206 cannot be led to receiving section 203 depending upon the orientation and contour of other organs in the proximity of the affected part in the body cavity.

SUMMARY OF THE INVENTION

An object of the present invention is to provide a ligation apparatus allowing ligation of a site in a body cavity extracorporeally with a small puncture in the somatic layer by using an elongated ligation apparatus in a deploying/withdrawing manner.

Another object of the present invention is to provide a ligation apparatus that can be introduced via the anus, the trachea, the urethra, and the like for ligation of an affected part without having to detach forceps or the ligation apparatus from the ligature.

A ligation apparatus of the present invention for achieving the above objects includes an opening portion at a front end portion of a rod in communication with the front end side, the left side, and the right side, having a cross section of substantially a U-shaped configuration in the direction of the axis of the rod, and a mobile unit inside the opening portion. The mobile unit includes a body held in a movable manner, and a thread supporting unit having a tip end portion protruding outward the front end of the opening portion for supporting a ligature at the tip end thereof.

According to the present structure, one end of the ligature is attached to the thread supporting unit of the mobile unit and the other end wound around the back of a site to be ligated in a predetermined direction of rotation. While a intermediate middle portion of the ligature is disposed at the upper face of the rod in the direction of rotation, the other end of the ligature is inserted into the opening portion in the predetermined direction of rotation to allow that other end of the ligature to transition from the upper side to the lower side. The ligature is pulled out from the opening portion to form a knot of the ligature at the ligation site.

The hole formed in the somatic layer can be reduced in size to alleviate the burden on the patient since a knot of the ligature can be tied at the end of a thin long rod for ligation of a site. Furthermore, the ligation apparatus can be introduced via the anus, the trachea, and the urethra, or the like for ligation of an affected part since the site can be ligated merely by maneuver of the tip end portion of the rod.

According to the ligation apparatus of the present invention, reliable ligation of a desired site can be carried out since a flexible insert member does not have to be inserted into a receiving section through a predetermined distance after passing through a curved portion of the main body as in the conventional ligation apparatus.

According to a preferable structure of the present invention, the upper side of the opening includes a ligature guiding face having a first slope face gradually inclining inward from the front end portion and a second slope face extending downwards to form an acute angle with the first slope. The tip end portion of the mobile unit is formed to be gradually distant from the front end with respect to the ligature guiding face.

According to the present structure, a great opening region is defined by the first slope face and the tip end portion of the mobile unit at the front end side of the ligation apparatus. Therefore, the ligature located at this opening portion is reliably guided to the upper side of the mobile unit. The ligature at the upper side of the mobile unit has its transition towards the opening portion prevented by the second slope face so that the ligature is led to the bottom side of the mobile unit. As a result, the ligation process can be carried out reliably.

According to a preferable structure of the present invention, a catch mechanism is provided at the upper face of the rod to catch the ligature when the intermediate portion of the ligature is disposed at the upper side of the rod.

The provision of such a catch mechanism allows the ligature to be easily translated from the upper face of the mobile unit to the bottom face while the ligature is arranged at the upper side of the rod. As a result, the ligation process can be carried out efficiently.

According to a preferable structure of the present invention, the catch mechanism includes a catch member provided inside the rod and rotatable about a predetermined center axis, allowing a protruding state from the surface of the rod and a retracting state accommodated within the rod, an operation shaft provided in the rod in a movable manner along the direction of the axis of the rod, having its tip end attached to the catch member in a rotatable manner for rotating the catch member by being moved axially forward/backward, and an actuator having the rod inserted at the proximal end side of the rod, and rotated along the circumference of the rod to provide forward/backward movement of the operation shaft.

According to the structure, the other end of the ligature can easily be inserted into the opening portion along the direction of rotation while the ligature is caught at the catch member which is protruding from the surface of the rod. After the ligature is pulled out from the opening, the catch member is accommodated within the rod using the actuator, whereby the retention of the ligature by the catch member is released to allow formation of a knot at the site for ligation.

Since the catch member can be retracted/deployed by means of the actuator provided at the proximal end side of the rod, the ligation process can be carried out more efficiently.

According to a preferable structure of the present invention, forceps grasping the ligature is provided at the other end of the ligature. Therefore, the ligature can be maneuvered more easily.

A ligation apparatus of present invention for achieving the above objects according to another aspect of the present invention includes a cut face formed at the front end of a rod, a mobile unit located on the cut face and having a hole for tying a ligature at the tip end, and a cover for holding the mobile unit in a movable manner together with the cut face, and attached to the rod so that a predetermined clearance is provided with respect to the cut face at the front end side, the left side, and the right side.

According to the ligation apparatus of the above structure, the ligature has one end tied to the hole of the mobile unit and the other end wound around the back of the ligation site in a predetermined direction of rotation. The other end of the ligature is inserted into the opening portion while an intermediate portion thereof is arranged at the upper side of the rod in the predetermined direction of rotation. The other end of the ligature is glided downwards from the upper side of the mobile unit and then pulled out from the opening, whereby a knot of the ligature is formed at the ligation site.

The foregoing and other objects, features, aspects and advantages of the present invention will become more apparent from the following detailed description of the present invention when taken in conjunction with the accompanying drawings.

BRIEF DESCRIPTION OF THE DRAWINGS

FIGS. 5–26 are diagrams for describing the ligation process by means of the ligation apparatus of FIG. 1.

DESCRIPTION OF THE PREFERRED EMBODIMENTS

Figure 1:
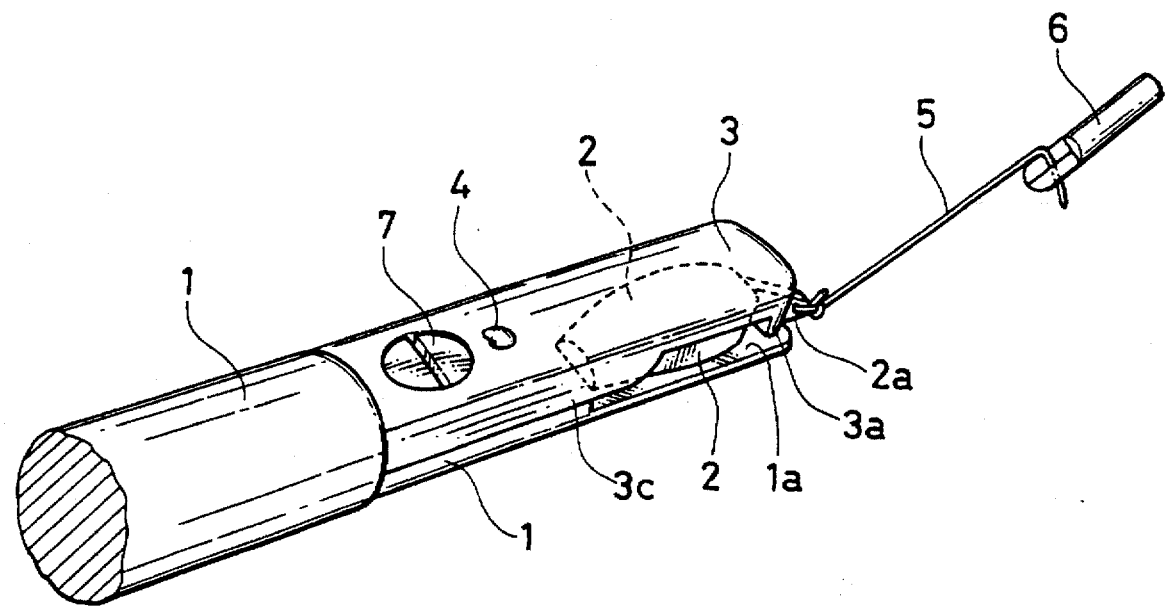
FIG. 1 is a perspective view showing a structure of a ligation apparatus according to a embodiment of the present invention.
Figure 2:
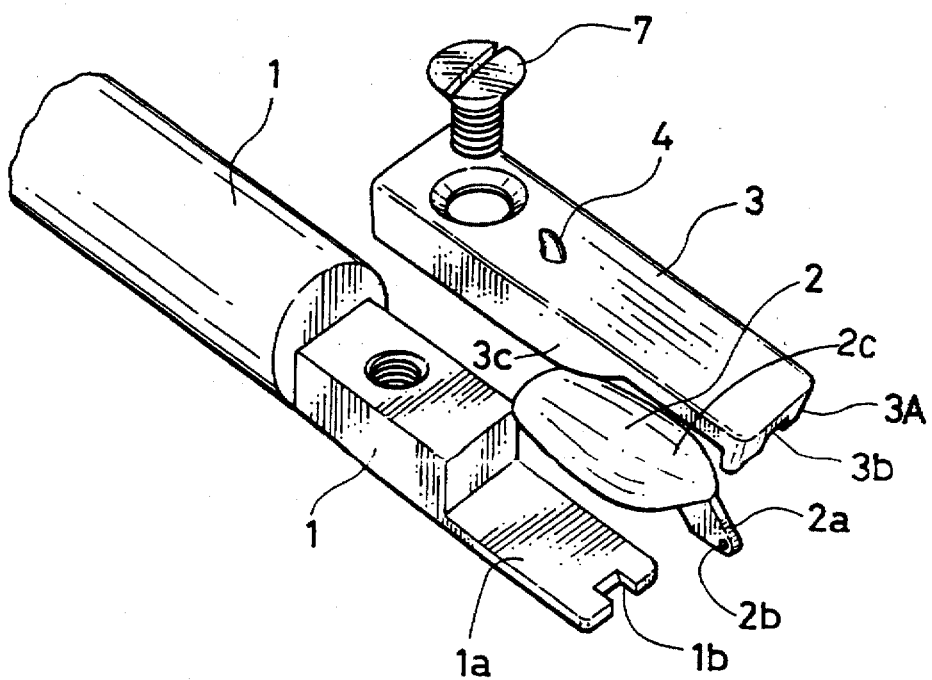
FIG. 2 is an exploded perspective view of the ligation apparatus of FIG. 1.

Embodiments of the present invention will be described hereinafter with reference to the drawings.

Referring to FIGS. 1–4, a ligation apparatus according to the present embodiment has a notch face 1a formed at the front end portion of a metal rod 1 of approximately 4 mm in diameter. A relatively heavy pillow-shaped mobile unit 2 is positioned on notch face 1a.

Mobile unit 2 is maintained in a rotatable manner by cover 3 of notch face 1a. The circumference of mobile unit 2 has a clearance substantially equal to the diameter of a ligature 5. Cover 3 is fixed to rod 1 by a screw 7. A horn-like catch mechanism 4 is provided at a predetermined position at the upper face of cover 3.

A ligature guiding face 3A is formed at the side end portion of cover 3. Ligature guiding face 3A includes a first slope face 3a gradually inclined inward from the front end portion, and a second slope face 3e extending downwards to form an acute angle with first slope face 3a. A cut groove 3b is formed in ligature guiding face 3A.

Mobile unit 2 has a main body 2c and a tapered end 2a provided at the tip end of main body 2c. A hole 2b for tying ligature 5 is provided at the leading edge portion of tapered end 2a.

A cut 1b is provided at the leading edge portion of notch face 1a.

Figure 3:
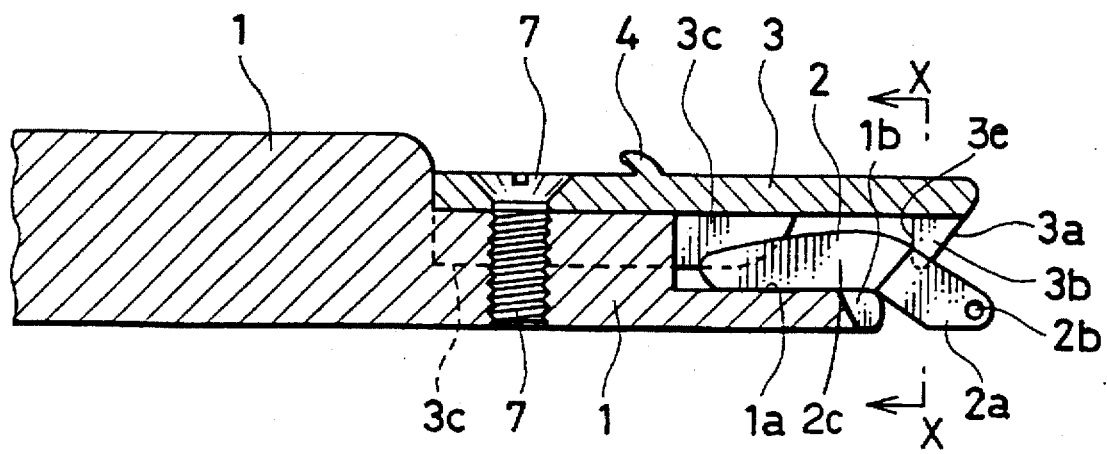
FIG. 3 is a sectional view of the ligation apparatus of FIG. 1 along the direction of axis thereof.
Figure 4:
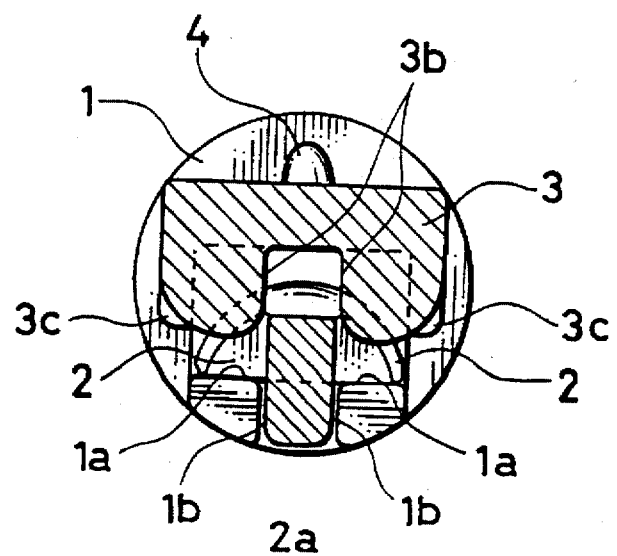
FIG. 4 is a sectional view of the ligation apparatus of FIG. 3 taken along the arrow line of X—X.

Mobile unit 2 is supported by notch face 1a and cover 3 as shown in FIGS. 3 and 4 with tapered end 2a protruding from cut groove 3b formed at the center of the end portion of ligature guiding face 3a and from cut 1b. Mobile unit 2 is held in a movable manner within a cavity defined by notch face 1a and cover 3. Mobile unit 2 is prevented from falling out from this cavity.

The dimension of mobile unit 2 is selected so that it has a clearance substantially equal to the diameter of ligature 5 in the cavity defined by notch face 1a, cover 3, and both side faces 3c of cover 3, and so that it can moves lightly in response to movement of ligature 5.

The operation of the ligation apparatus of the above-described structure is set forth in the following with reference to FIGS. 5–34.

Figure 5:
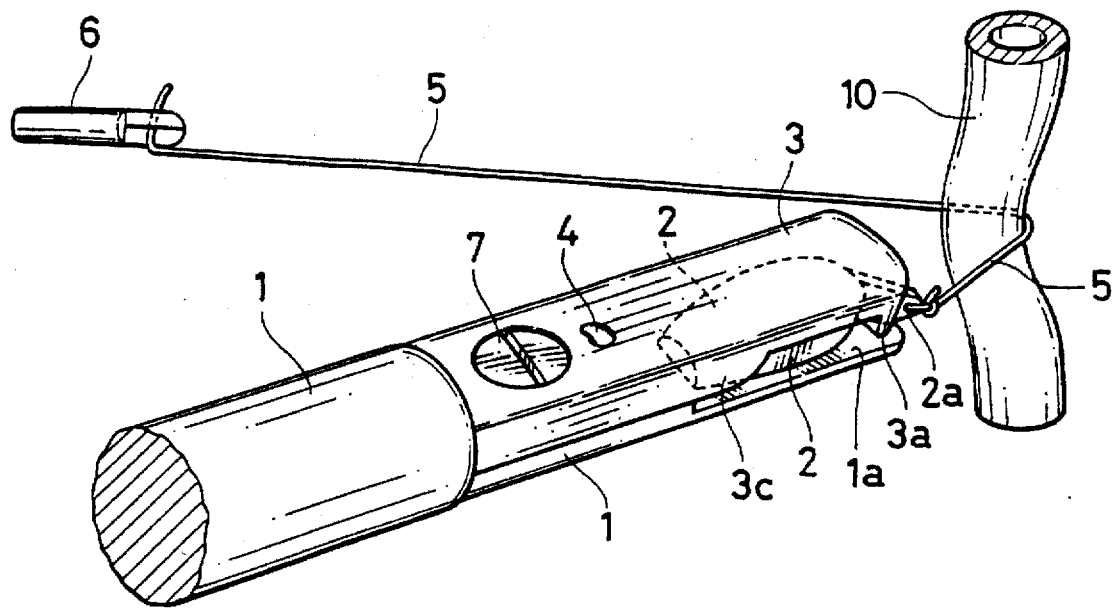

Referring to FIG. 5, ligature 5 having one end tied to tapered end 2a of mobile unit 2 of the ligation apparatus has the other end threaded behind the proximity of an affected portion such as a blood vessel site in an arc manner and is clasped with forceps 6. This corresponds to the state shown in FIG. 27.

Figure 6:
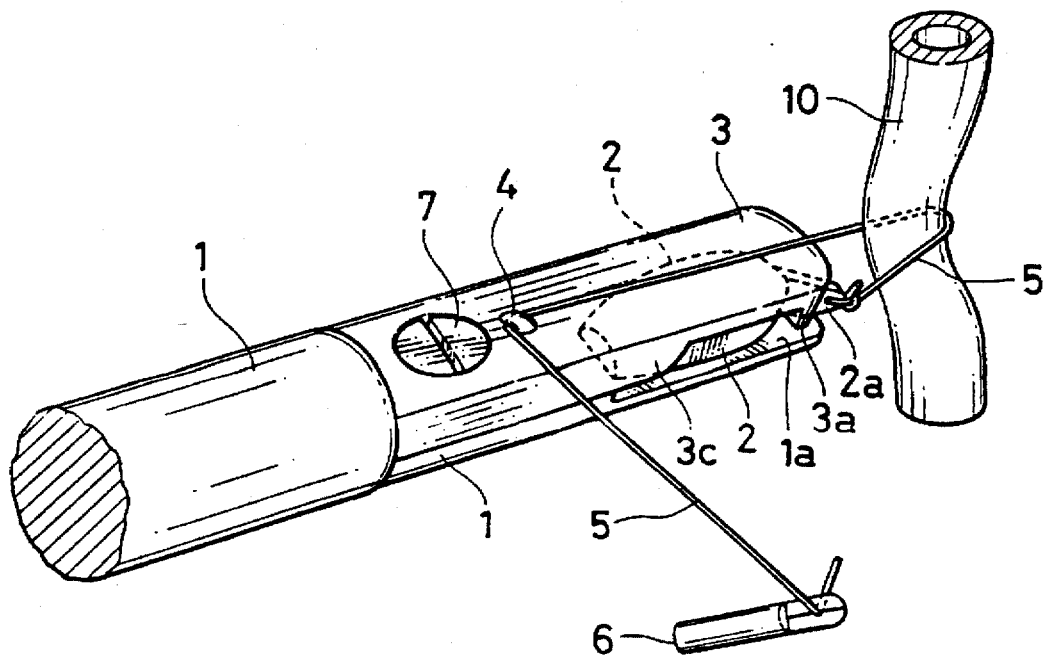

Referring to FIG. 6, ligature 5 is retained by catch 4 provided at the upper face of the ligation apparatus, whereby ligature 5 wound around affected part 10 forms an elongated loop. This corresponds to the state shown in FIG. 28.

Figure 7:
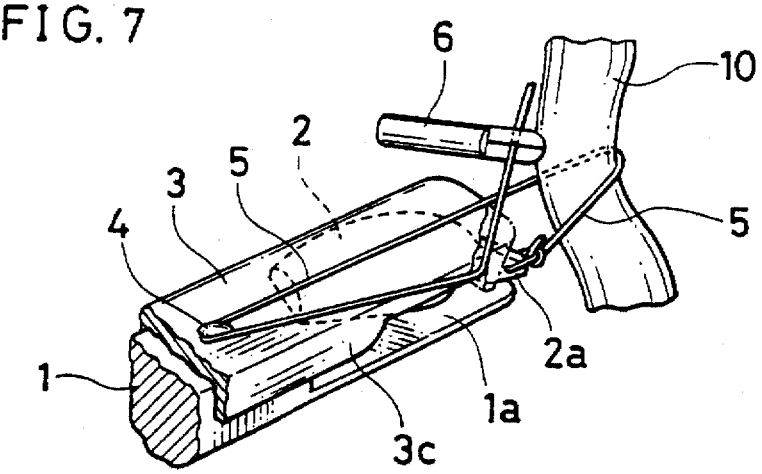
Figure 8:
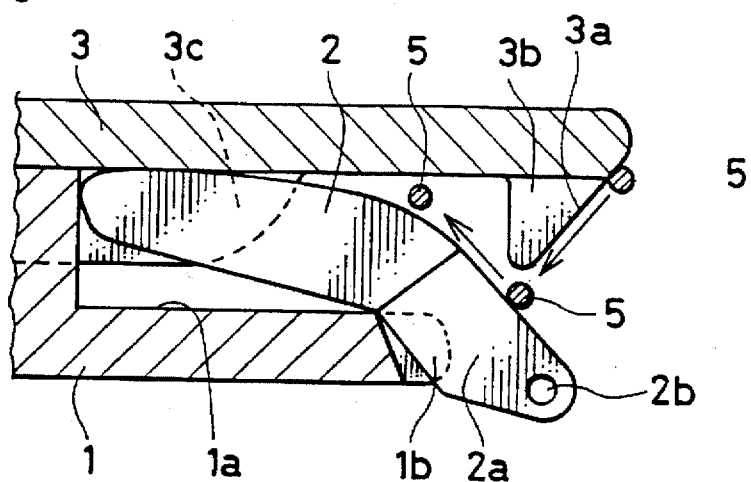
Figure 9:
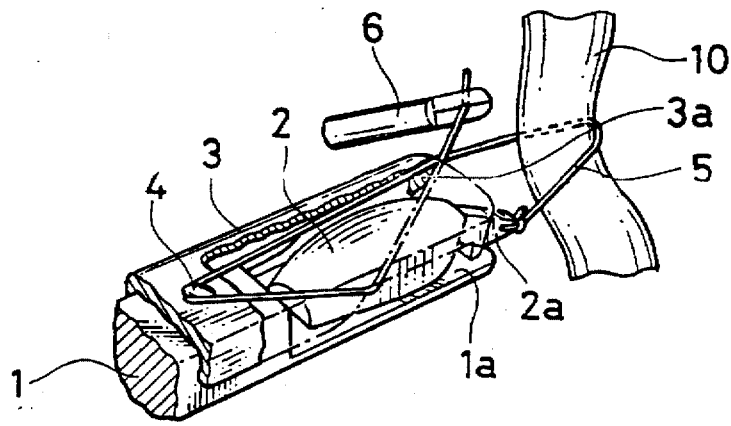
Figure 10:
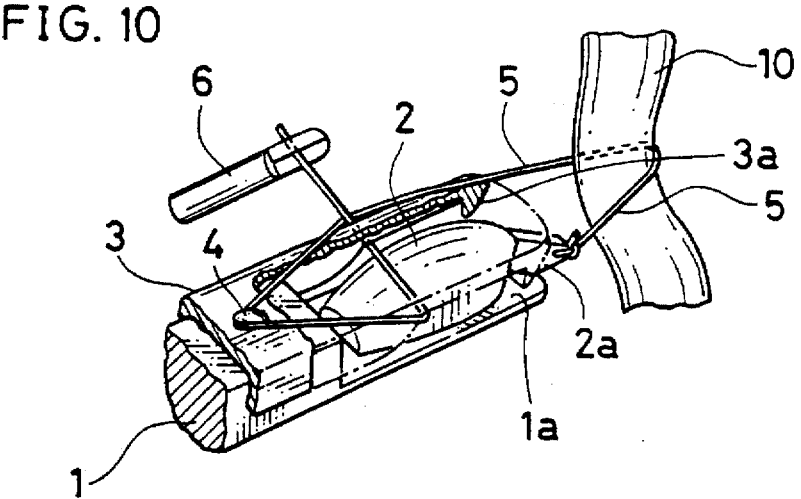
Figure 11:
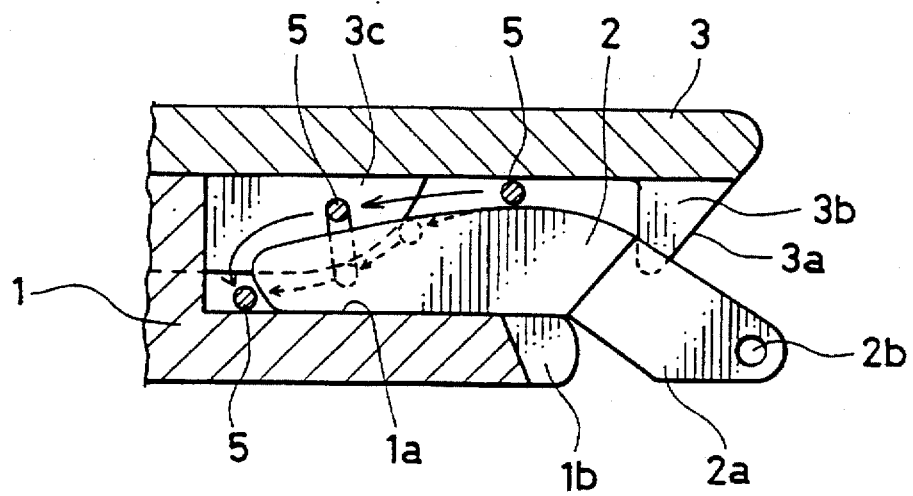
Figure 12:
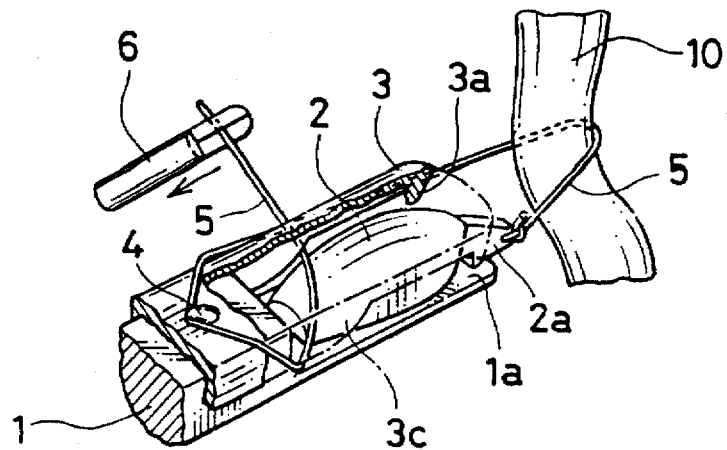
Figure 13:
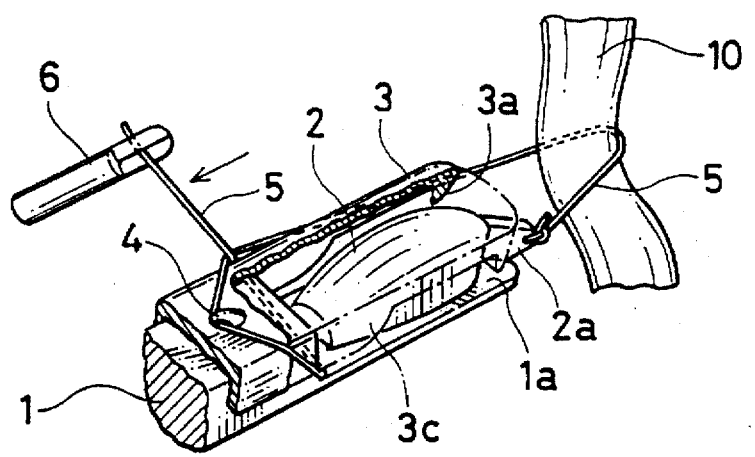

Referring to FIG. 7, ligature 5 is glided along the side of cover 3 and then along ligature guiding face 3A, whereby an intermediate portion of ligature 5 enters cover 3 to slide on the upper face of tapered end 2a of mobile unit 2 as shown in FIG. 8. This corresponds to the state shown in FIG. 29.

Referring to FIGS. 9–13, ligature 5 is translated between the inner face of cover 3 and the upper face of mobile unit 2, whereby ligature 5 is positioned on notch face 1a at the rear portion of mobile unit 2.

Detachment of mobile unit 2 out from the opening portion is prevented since mobile unit 2 has tapered end 2a supported by cut groove 3b of cover 3 and cut 1b of notch face 1a, and motion of the rear side portion of mobile unit 2 is restricted within the side faces 3c of cover 30. This corresponds to the state shown in FIG. 30.

Figure 14:
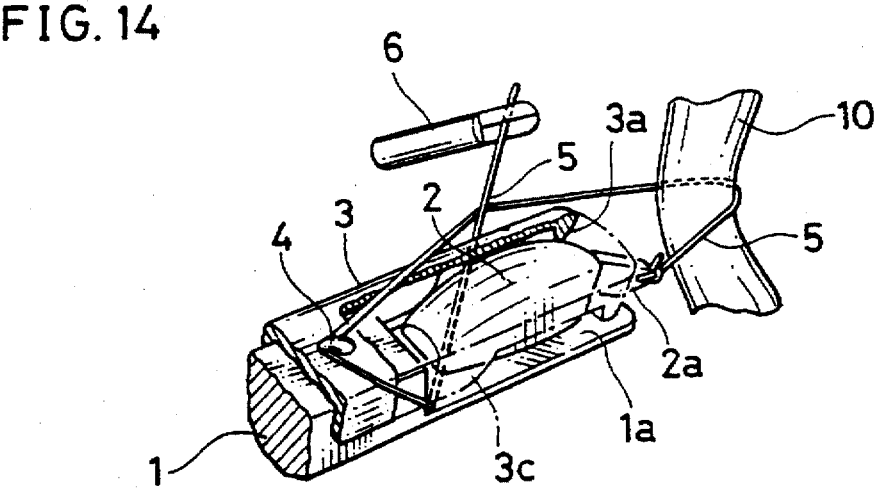
Figure 15:
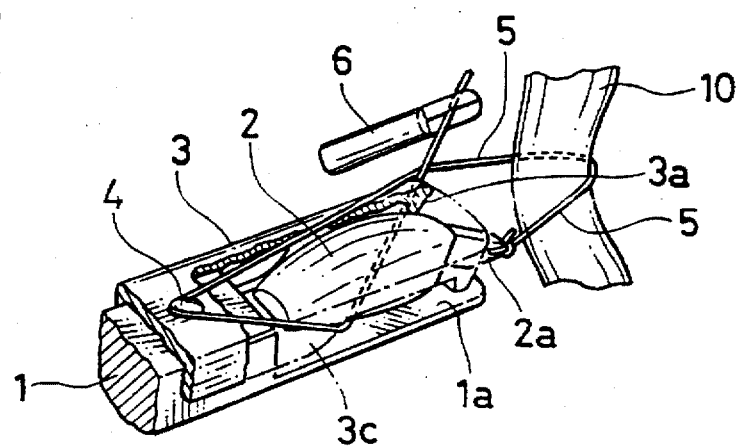
Figure 16:
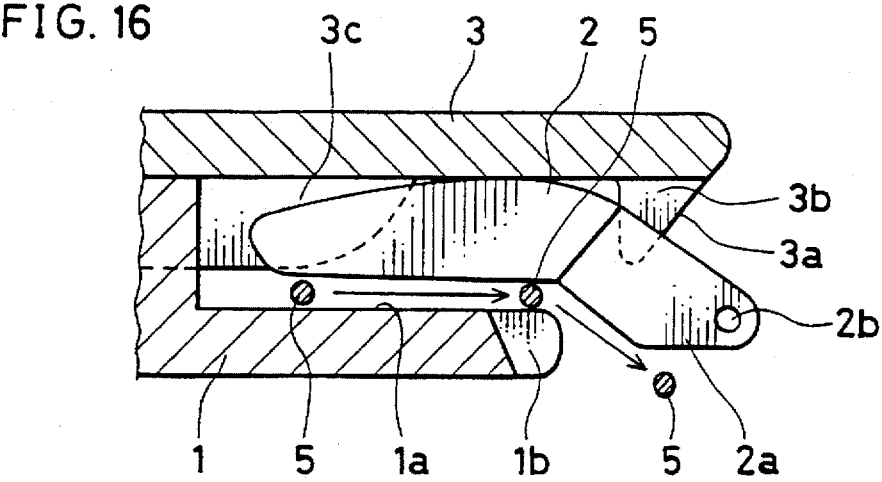

Referring to FIGS. 14–16, ligature 5 is translated between the upper face of notch face 1a and the bottom face of mobile unit 2 and advanced in a forward direction (towards the distal end) by forceps 6. This corresponds to the state shown in FIGS. 31 and 32.

Figure 17:
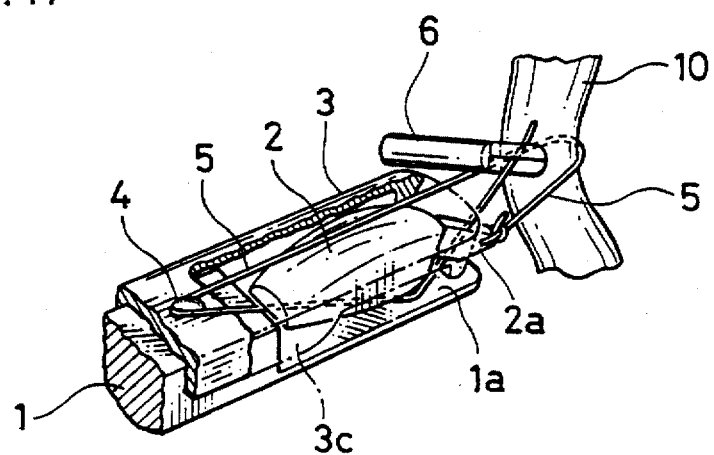
Figure 18:
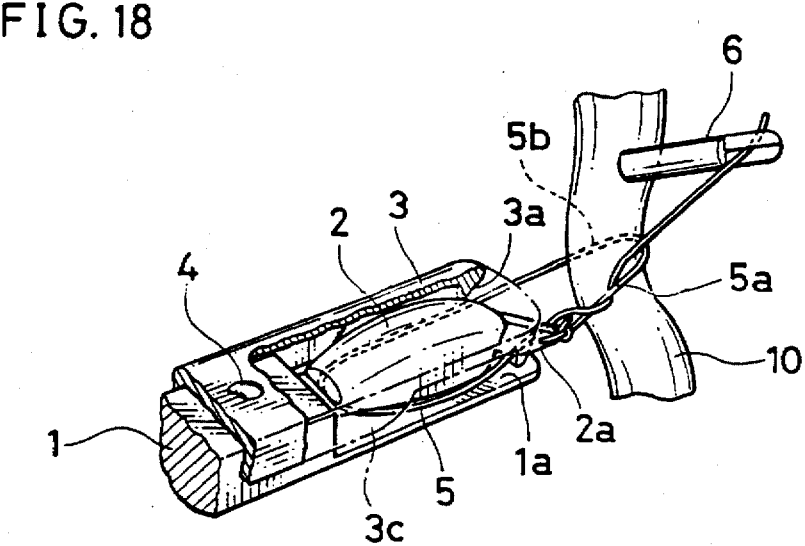
Figure 23:
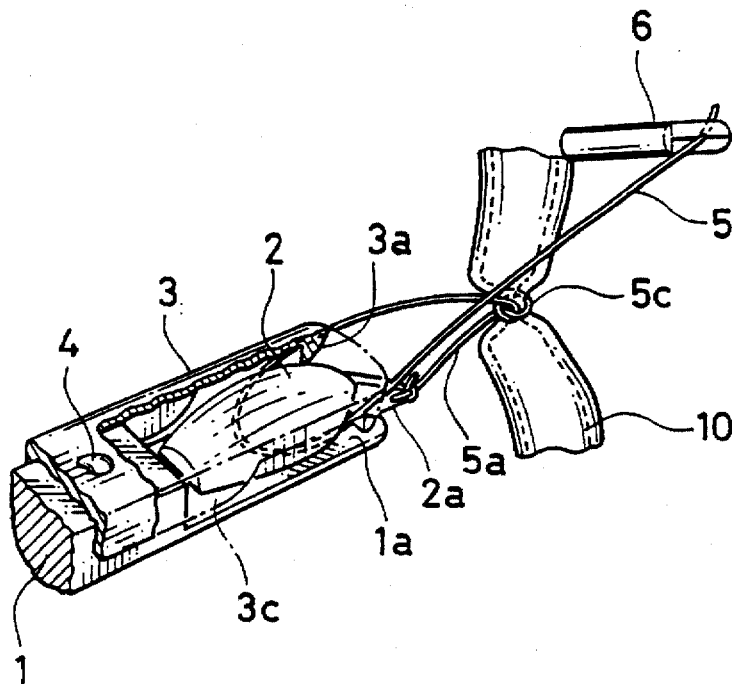
Figure 24:
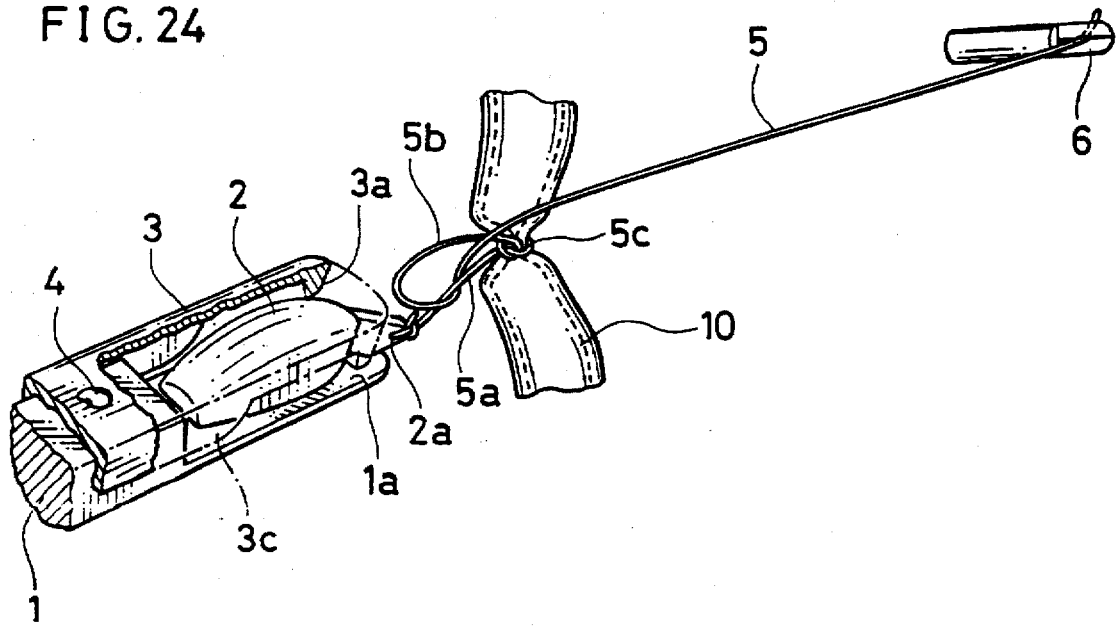
Figure 25:
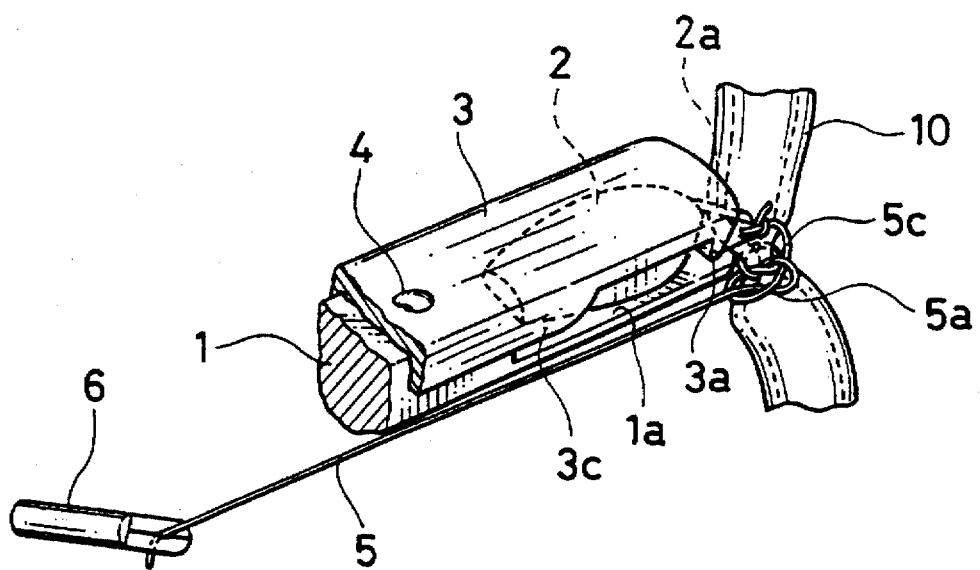
Figure 26:
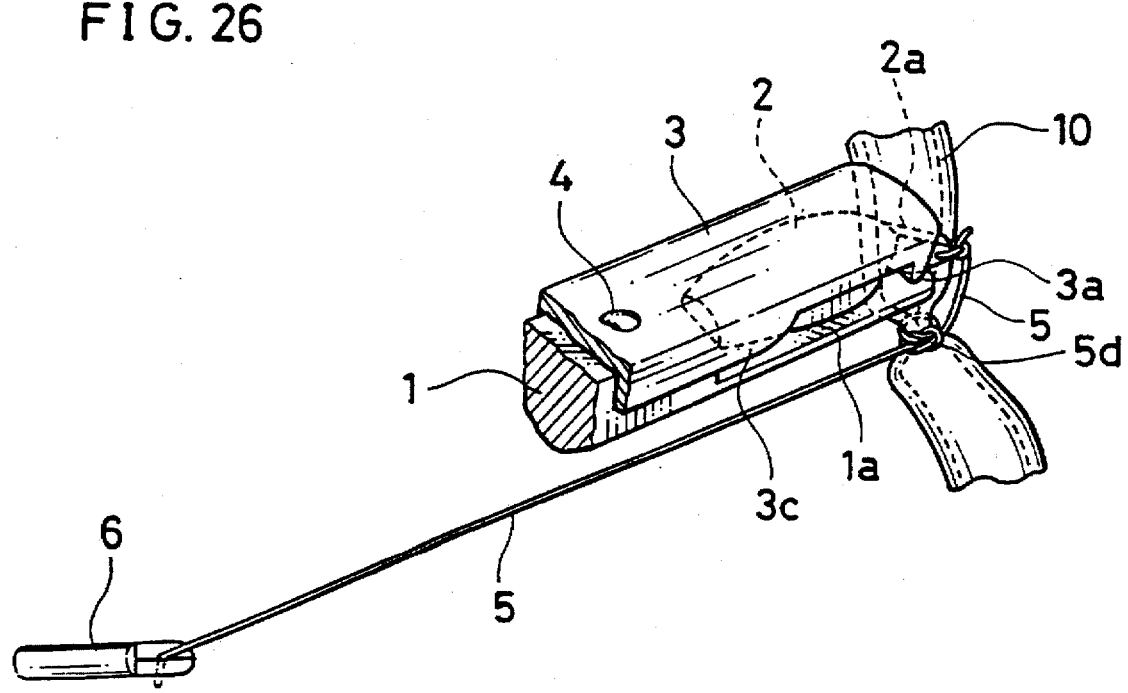
Figure 27:
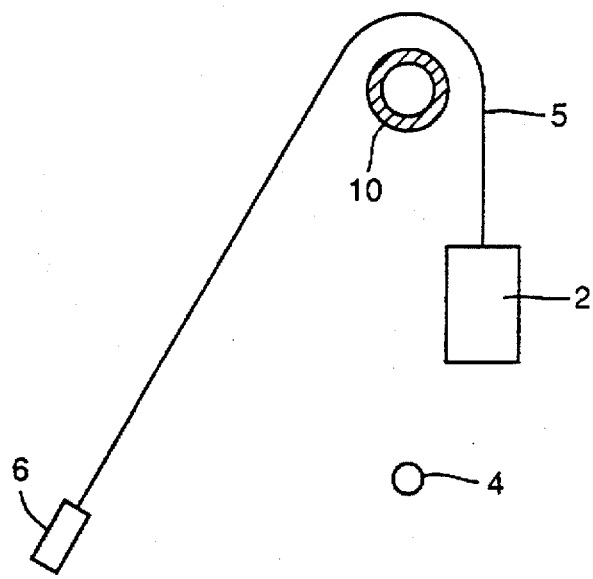
FIGS. 27–34 are schematic diagrams for describing the ligation process by means of the ligation apparatus of FIG. 1.
Figure 28:
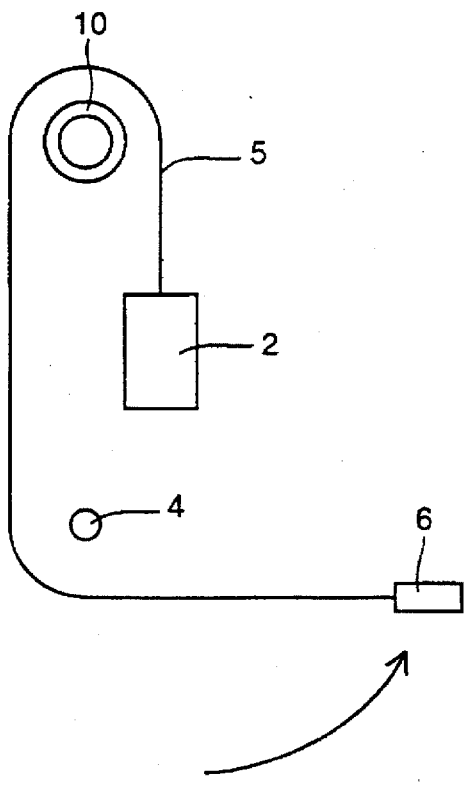
Figure 29:
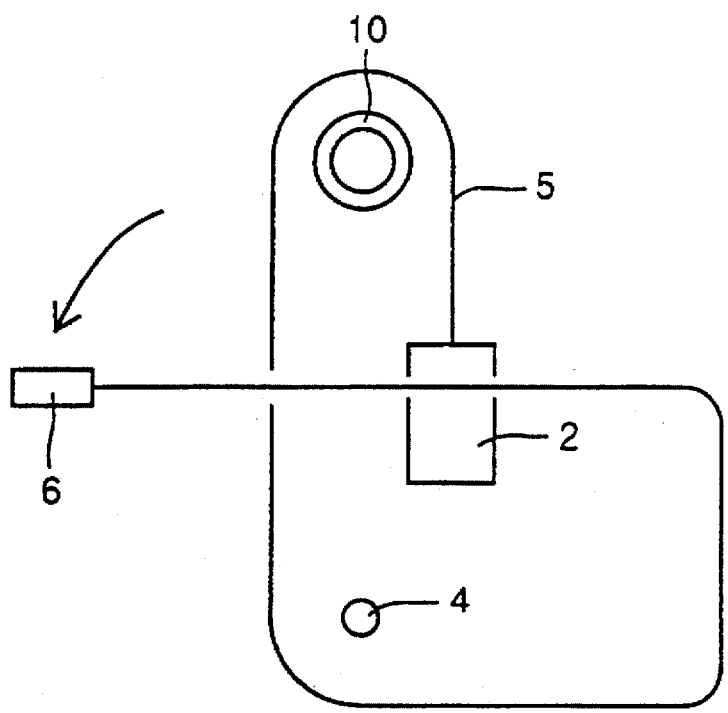
Figure 30:
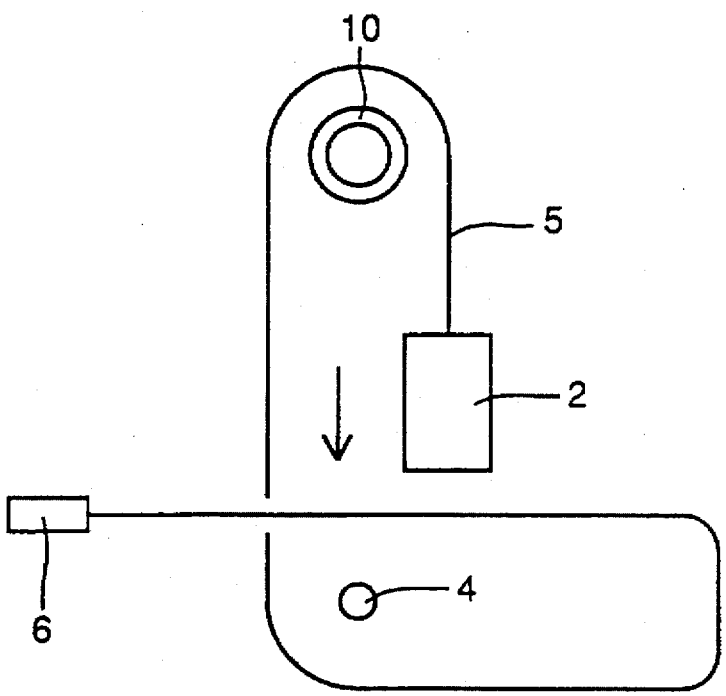
Figure 31:
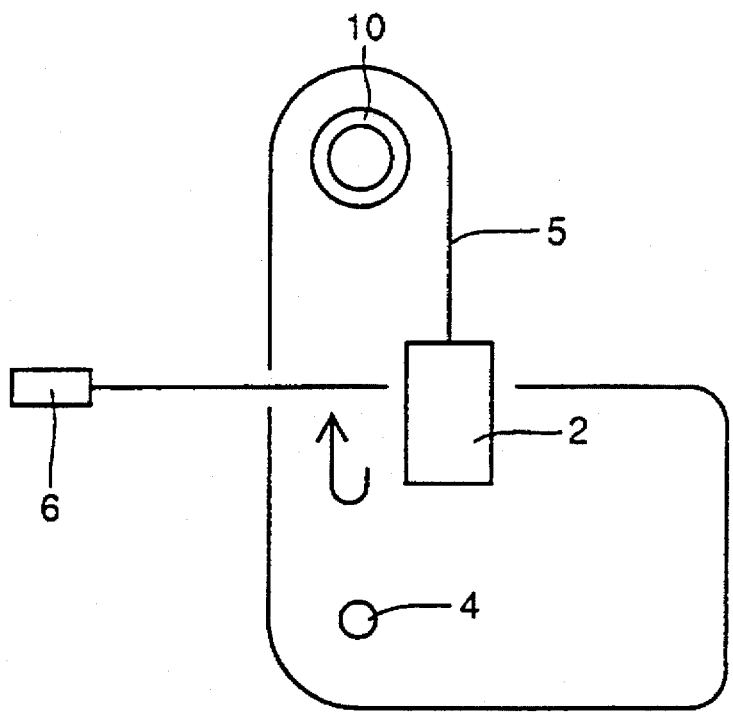
Figure 32:
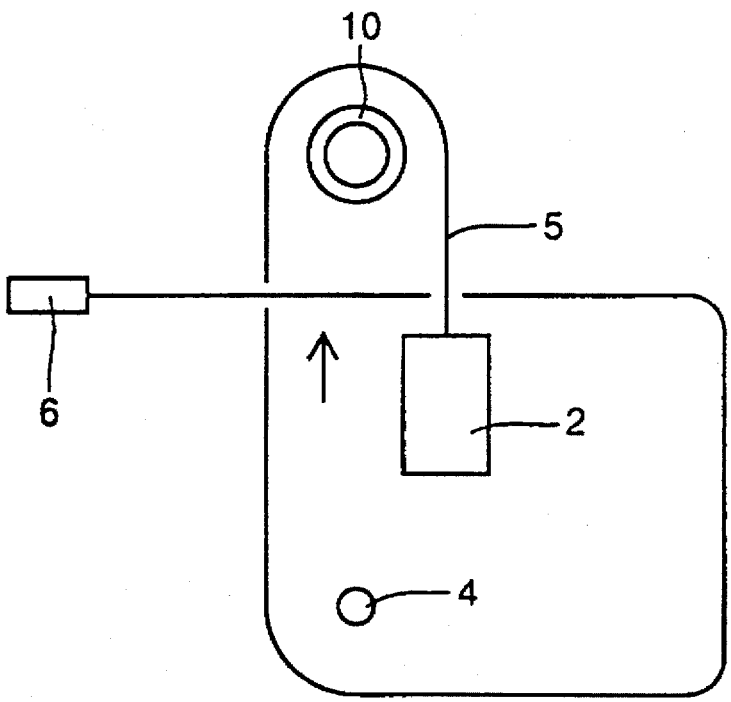
Figure 33:
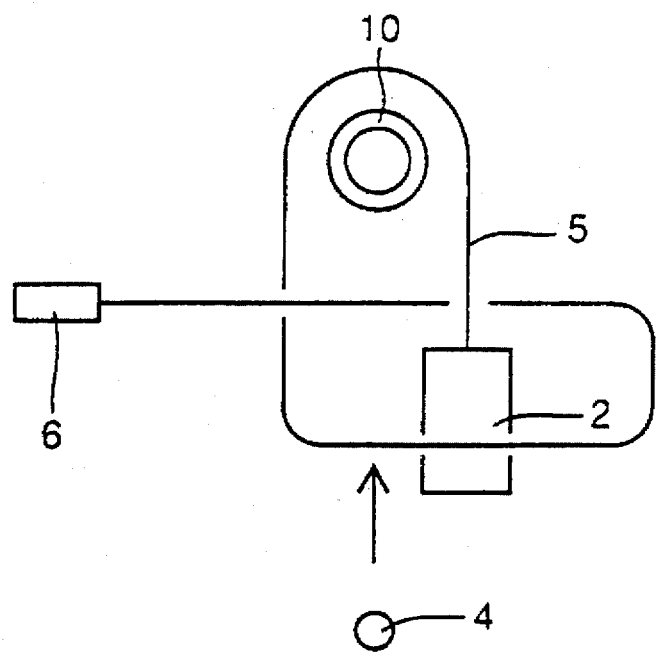
Figure 34:
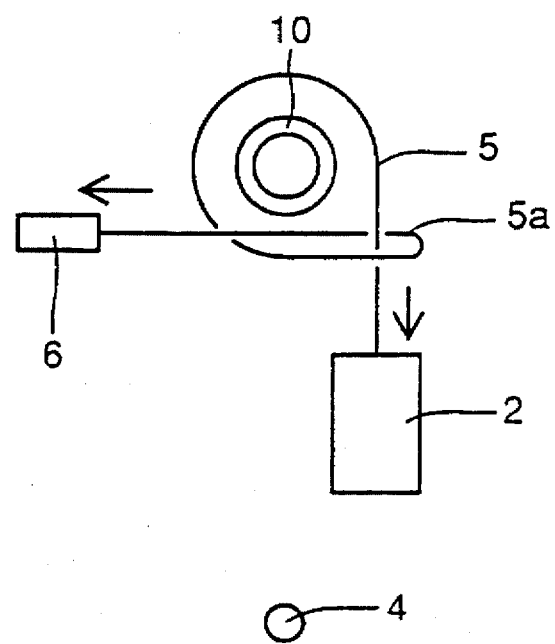

Referring to FIG. 17, ligature 5 is pulled in a direction so as to come out from notch face 1a, and the catch by catch member 4 of ligature 5 is released. This corresponds to the state shown in FIG. 33. Then, ligature 5 is pulled in a direction to run out from notch face 1a using forceps 6, whereby a loop 5b having a twist 5a which becomes a knot as shown in FIG. 18 is formed. This corresponds to the state shown in FIG. 34.

Referring to FIGS. 19–21, ligature 5 is pulled in a direction indicated by the arrow in the drawing so as to narrow loop 5b, and a single knot 5c securely binding affected site 10 is formed. Since there is a possibility that single knot 5c may be untied or unloosened, the other end of ligature 5 is once more caught at catch mechanism 4 to repeat a procedure similar to the above-described steps to form an elongated loop again, resulting in a new knot over single knot 5c, as shown in FIGS. 22–26. Thus, a ligated portion 5d by a double knot that is not easily unloosened by an external force is formed.

According to the above-described embodiment, a site can be easily ligated by using mobile unit 2 provided at the front end portion of rod 1.

Another embodiment of the present invention will be described hereinafter.

A ligation apparatus 100 of the present embodiment has a catch mechanism 4 accommodated within a rod by proximal manual operation.

The schematic structure of ligature apparatus 100 will be described with reference to FIG. 35.

A grip rod 101 includes a fixed sleeve 102 having a wave-like concave and convex edge 102a and a rotatable sleeve 103 having a wave-like concave and convex edge 103a corresponding to wave-like concave and convex edge 102a. A cover 104 is provided upper of rotatable sleeve 103. A rod 105 extends from the one end of cover 104 opposite rotatable sleeve 103. A ligator of a structure similar to that of the above-described embodiment is attached at the leading edge (distal end) of rod 105.

The internal structure of ligation apparatus 100 will be described with reference to FIG. 36.

Catch mechanism 4 is provide in rod 105 in a rotatable manner about a center shaft 4a. Catch mechanism 4 attains an accommodated state in FIG. 36.

An operation shaft 107a is provided in rod 105 in a slidable manner along the direction of axis of rod 105, and has its end attached to catch mechanism 4 in a rotatable manner by a shaft 4b. Operation shaft 107a functions to rotate catch mechanism 4 about shaft 4a by being slided backward/forward along the direction of axis of rod 105.

At the rear end (proximal end) portion of operation shaft 107a, a spring 108 is provided at the rear edge portion of rod 105 to be biased backwards towards fixed sleeve 102.

Fixed sleeve 102 is fixed to grip rod 101 by means of a small screw 102A. Rotatable sleeve 103 is attached in a rotatable manner with respect to grip rod 101. Cover 104 is fixed to operation shaft 107a by means of a small screw 106A. An elongated hole 105n is provided at the outer circumference of rod 105 to allow a slidable motion with respect to rod 105.

By rotating rotatable sleeve 103, rotatable sleeve 103 is pushed towards the tip end side (distal end) by the interaction of wave-like concave and convex edges 102a and 103a of fixed sleeve 102 and rotatable sleeve 103, respectively. This movement of rotatable sleeve 103 causes cover 104 to be translated towards the distal end.

Figure 37:
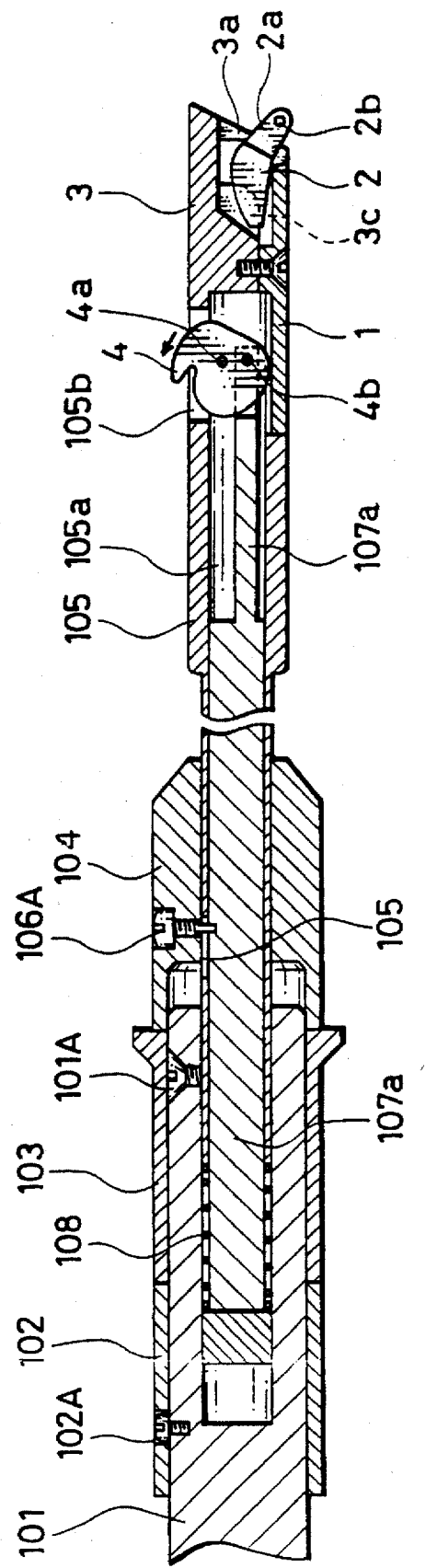
Figure 38:
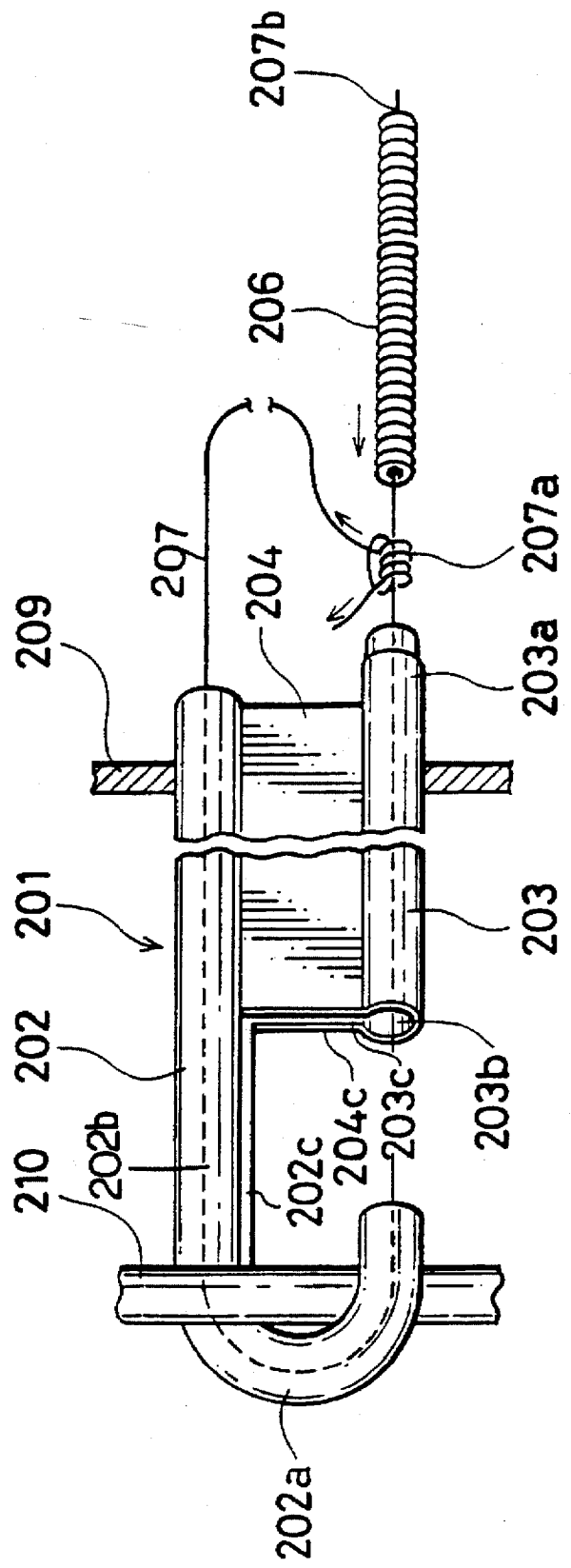
FIG. 38 shows a conventional ligation apparatus.

Since cover 104 is fixed to operation shaft 107a by small screw 106A, operation shaft 107a moves towards the distal end against the bias force of spring 108. As a result, catch mechanism 4 rotates about shaft 4a in a direction indicated by the arrow in FIG. 37, whereby catch mechanism 4 protrudes from the surface of rod 105.

Figure 35:
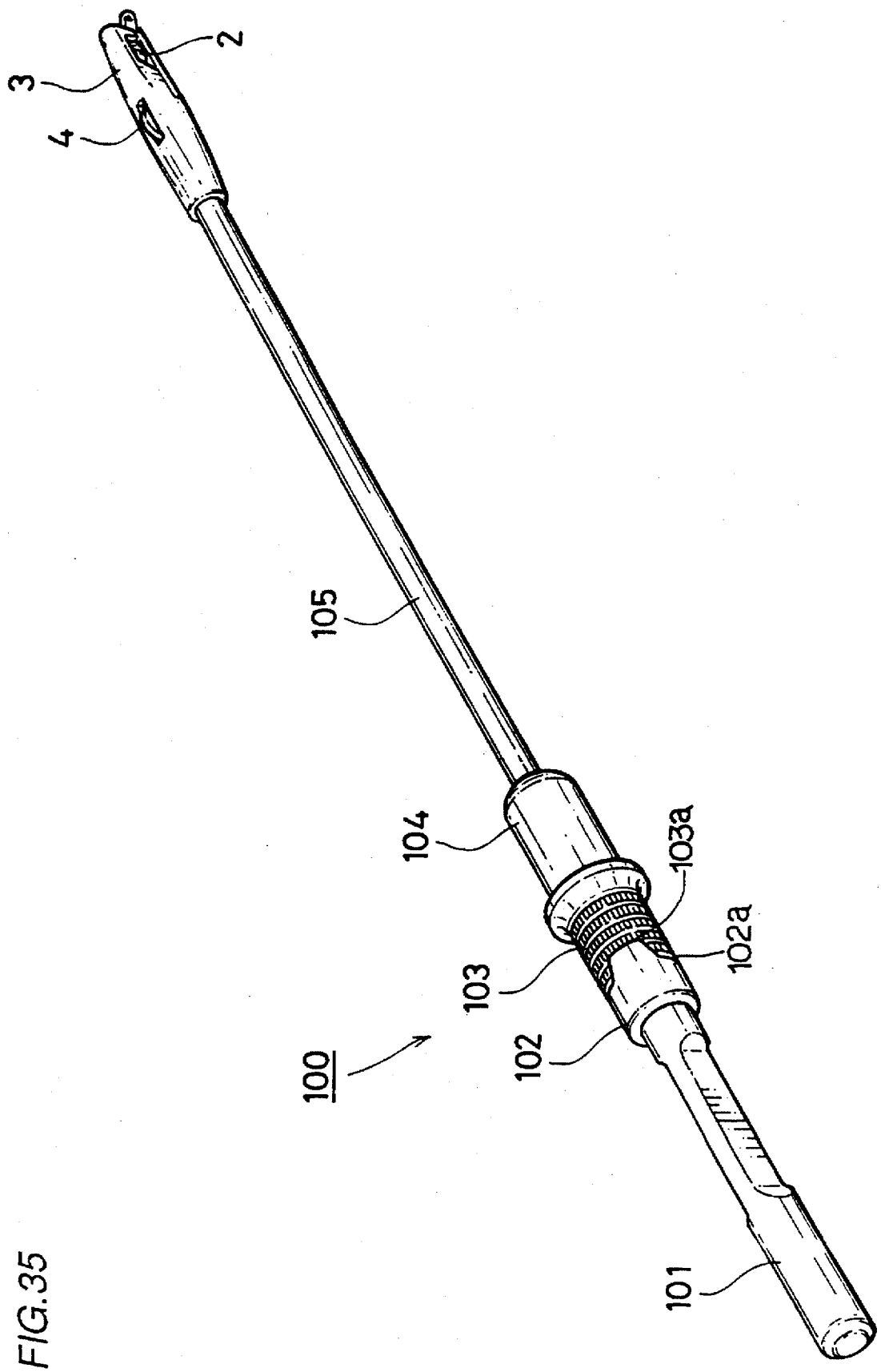
FIG. 35 is a perspective view showing a structure of a ligation apparatus according to another embodiment of the present invention.
Figure 36:
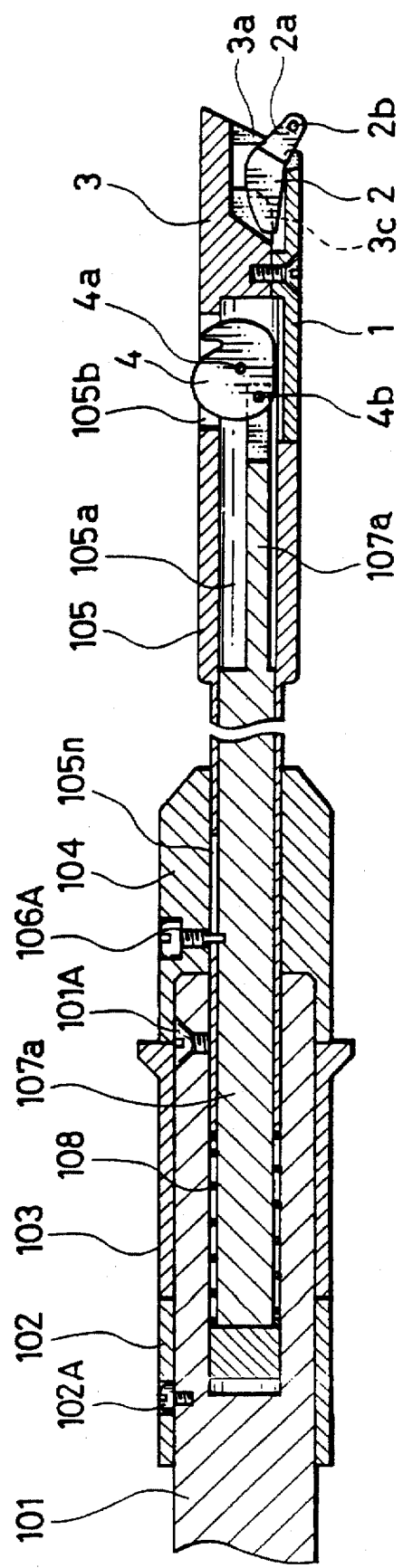
FIGS. 36 and 37 are sectional views of the ligation apparatus of FIG. 35 showing a first state and a second state, respectively.

When rotatable sleeve 103 is further rotated, operation shaft 107a returns to the former state shown in FIGS. 35 and 36 since a force is constantly exerted to return towards direction of grip rod 101.

Since operation of catch mechanism 4 can be effected in a proximal manner Using the ligation apparatus of the above-described structure, so that the ligation process of a site can be facilitated.

It will be understood that the above-described embodiments of the present invention are merely examples of embodying the present invention, and other various forms may be employed which come within the meaning and range of equivalency of the claim to be embraced within the scope.

Although the present invention has been described and illustrated in detail, it is clearly understood that the same is by way of illustration and example only and is not to be taken by way of limitation, the spirit and scope of the present invention being limited only by the terms of the appended claims.

What is claimed is:

1. A ligation apparatus comprising:
   a) a rod having an opening at a distal end thereof, the opening further comprising a cavity, a distal end opening, a left side opening and a right side opening; and
   b) a mobile unit inside said cavity and including a body held in a movable manner in said cavity and a thread supporting unit having a tip end portion protruding through the distal end opening for supporting a ligature at said tip end portion;
   wherein said thread supporting unit of said mobile unit is adapted to have one end of a ligature tied thereto with an opposite end of the ligature for winding around a back of a ligation site in a predetermined direction of rotation, and said opening is adapted to receive the opposite end of the ligature in said predetermined direction of rotation with an intermediate portion of said ligature disposed at an upper surface side of said rod in said predetermined direction of rotation, and further wherein an upper side of said mobile unit is adapted to guide the opposite end of the ligature downward so that said ligature can be pulled out from under said mobile unit and from said opening whereby a knot of said ligature is formed at said ligation site.

2. The ligation apparatus according to claim 1, wherein the distal end of said rod includes a ligature guiding face having a first slope gradually inclining inward from the distal end, and a second slope extending downwards so as to form an acute angle with said first slope,
   wherein said tip end portion of said mobile unit is formed to be gradually distant from said ligature guiding face in a direction towards said distal end.

3. The ligation apparatus according to claim 1, wherein a catch device is provided at the upper surface side of said rod for catching said ligature when the intermediate portion of said ligature is disposed at the upper surface side of said rod.

4. The ligation apparatus according to claim 3, wherein said device comprises
   a catch member provided in said rod in a rotatable manner about a predetermined center axis, allowing a protruding state and an accommodated state,
   an operation shaft provided in said rod in a slidable manner along a direction of a longitudinal axis of said rod, having one end attached to said catch member in a rotatable manner for rotating said catch member by being moved backwards and forwards axially, an
   an actuator having a proximal end of said rod inserted therein for moving said operation shaft backwards and forwards by being rotated along the circumference of said rod.

5. The ligation apparatus according to claim 1, wherein forceps for grasping said ligature is provided at the opposite end of said ligature.

6. A ligation apparatus comprising:
   a notch face formed at a front end of a rod,
   a mobile unit placed on said notch face, including a hole to which a thread for ligation is tied at the tip end thereof, and
   a cover for holding said mobile unit in a movable manner with said notch face, attached to said rod so as to form an opening portion having a predetermined clearance from said notch face at a front side, a left side, and a right side,
   wherein said mobile unit is adapted to have one end of a ligature tied thereto, with an opposite end of the ligature for winding around a back of a ligation site in a predetermined direction of rotation, and said opening is sized to receive the opposite end of the ligature in said direction of rotation with an upper surface side of said rod adapted to receive an intermediate portion of the ligature in said direction of rotation, and further wherein an upper side of said mobile unit is adapted to guide the opposite end of the ligature downwards so that said ligature can be pulled out from under said mobile unit and from said opening, whereby a knot of said ligature is formed at said ligation site.

* * * * *